(12) United States Patent
Eriksson et al.

(10) Patent No.: US 9,371,275 B2
(45) Date of Patent: Jun. 21, 2016

(54) 5-AMINOLEVULINIC ACID PRODRUGS FOR USE IN PHOTODYNAMIC THERAPY AND PHOTODYNAMIC DIAGNOSIS

(71) Applicant: Swedish Pharma AB, Örebro (SE)

(72) Inventors: Leif A. Eriksson, Göteborg (SE); Lennart Löfgren, Örebro (SE)

(73) Assignee: SWEDISH PHARMA AB, Orebro (SE)

( * ) Notice: Subject to any disclaimer, the term of this patent is extended or adjusted under 35 U.S.C. 154(b) by 0 days.

(21) Appl. No.: 14/077,469

(22) Filed: Nov. 12, 2013

(65) Prior Publication Data
US 2014/0100271 A1 Apr. 10, 2014

Related U.S. Application Data

(62) Division of application No. 13/061,340, filed as application No. PCT/SE2009/050988 on Sep. 1, 2009, now abandoned.

(60) Provisional application No. 61/136,369, filed on Sep. 2, 2008.

(30) Foreign Application Priority Data

Sep. 1, 2008 (SE) ........................ 0801887

(51) Int. Cl.
| | | |
|---|---|---|
| *C07C 271/22* | (2006.01) | |
| *C07D 317/30* | (2006.01) | |
| *A61K 45/06* | (2006.01) | |
| *A61K 31/22* | (2006.01) | |
| *A61K 31/357* | (2006.01) | |
| *C07C 251/00* | (2006.01) | |
| *A61K 31/27* | (2006.01) | |
| *A61K 31/325* | (2006.01) | |
| *A61K 41/00* | (2006.01) | |
| *C07C 251/06* | (2006.01) | |
| *C07C 251/38* | (2006.01) | |

(52) U.S. Cl.
CPC ............... *C07C 271/22* (2013.01); *A61K 31/22* (2013.01); *A61K 31/27* (2013.01); *A61K 31/325* (2013.01); *A61K 31/357* (2013.01); *A61K 41/0061* (2013.01); *A61K 45/06* (2013.01); *C07C 251/00* (2013.01); *C07C 251/06* (2013.01); *C07C 251/38* (2013.01); *C07D 317/30* (2013.01)

(58) Field of Classification Search
CPC . A61K 31/27; A61K 31/325; A61K 41/0061; A61K 31/22; A61K 31/357; A61K 45/06; C07C 251/06; C07C 251/38; C07C 271/22; C07C 251/00; C07D 317/30
See application file for complete search history.

(56) References Cited

U.S. PATENT DOCUMENTS

| 5,661,111 A | 8/1997 | Kuramochi et al. |
| 6,034,267 A | 3/2000 | Gierskcky et al. |
| 2003/0093057 A1* | 5/2003 | Zhang et al. .................. 604/500 |

FOREIGN PATENT DOCUMENTS

| DE | 10312659 A1 | 10/2004 |
| WO | 96/28412 A1 | 9/1996 |
| WO | 0210120 A1 | 2/2002 |

OTHER PUBLICATIONS

Jaffe et al., "Nitrogen-15 and carbon-13 NMR studies of ligands bound to the 280 000-dalton protein porphobilinogen synthase elucidate the structures of enzyme-bound product and a Schiff base intermediate", Part of Biochemistry, 1990, vol. 29, No. 36, pp. 8345-8350, p. 8346, right column, line 64-p. 8347, left column, line 20, table II, p. 8347.
Kloek et al., "Prodrugs of 5-aminolevulinic acid for photodynamic therapy", Part of: Photochemistry and Photobiology, 1996, vol. 64, No. 6, pp. 994-1000, the whole document.
Kaliszewski et al., "Formation of protoporphyrin IX from carboxylic and amino-derivatives of 5-aminolevulinic acid", Part of: Photodiagnosis and Photodynamic Therapy, 2005, vol. 2, No. 2, pp. 129-134, the whole document.
Stable isotope overview [retrieved Feb. 12, 2013]. Retrieved from the Internet <URL: http://sisbl.uga.edu/stable.html>.
Iinuma et al., "A mechanistic study of cellular photodestruction with 5-aminolaevulinic acid-induced prophyrin", Br. J. Cancer, 1994, vol. 70, pp. 21-28.

(Continued)

*Primary Examiner* — Anoop Singh
*Assistant Examiner* — Doan Phan
(74) *Attorney, Agent, or Firm* — Bacon & Thomas, PLLC

(57) ABSTRACT

There is provided a compound of Formula (I)

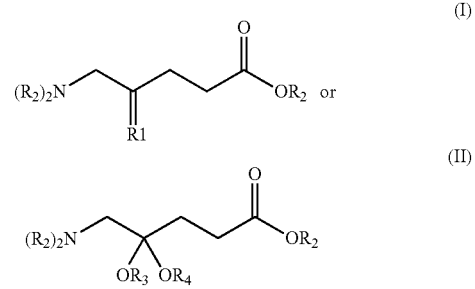

and salts thereof, where $R_1$ is an oxime or an alkylated oxime; the alkylated oxime comprises a linear or branched alkyl group of length C1 to C5; and $R_2$ are each independently (a) an unsubstituted or substituted linear or branched alkyl group of chain length $C_{1-7}$, (b) an aryl substituted alkyl group, where the aryl group is substituted, (c) an alkoxy substituted alkyl group, where the alkoxy group is substituted by a methoxy group or an alkoxy group substituted with an alkoxy group, or (d) an H atom, where the substituents in (a) and (b) are hydroxy, alkoxy, acyloxy, alkoxycarbonyloxy, amino, aryl, nitro, oxo or fluoro groups. The compounds may be used as a medicament.

21 Claims, 2 Drawing Sheets

(56) References Cited

OTHER PUBLICATIONS

Hans-Ulrich Meisch et al., "Determination of 5-Aminolevulinic Acid in Biological Samples by High-Performance Liquid Chromatography", Analytical Biochemistry, vol. 149, No. 1, 1985, XP024828403, pp. 29-34.

"Imine", Wikipedia, Apr. 2015, XP055190127, retrieved from the Internet: http://en.wikipedia.org/wiki/Imine, pp. 1-3.

A. Windaus et al., "Ueber das Verhalten einiger aus Imidazolen bereiteter Bis-[acyl-amino]-athylen-Derivate", Aus. d. Allgem. Chem. Laboratorium d. Universitat Gottingen, vol. 54, No. 10, 1921, pp. 2745-2755, XP-002244972.

L. Pichat et al., "Synthese du chlorhydrate de l'acide delta-aminolevulique Marque par les isotopes I-chlorhydate d'acid delta-aminolevulique 13N", Bulletin de la Societe Chimique de France, 1956, pp. 1750-1751, XP009008600.

S. Gacond et al., "Synthesis of Bisubstrate Inhibitors of Prophobilinogen Synthase from Pseudomonas aeruginosa", Chemistry & Biodiversity, vol. 4, No. 2, 2007, pp. 189-202, XP55189977.

Extended European Search Report of corresponding European Application No. 09810325.2 dated Jun. 1, 2015.

Supplementary European Search Report of corresponding European Application No. 09810325 dated May 19, 2015.

* cited by examiner

5-AMINOLEVULINIC ACID PRODRUGS FOR USE IN PHOTODYNAMIC THERAPY AND PHOTODYNAMIC DIAGNOSIS

CROSS REFERENCE TO RELATED APPLICATIONS

This application is a divisional of U.S. patent application Ser. No. 13/061,340, filed May 16, 2011, which is a 371 of International Application No. PCT/SE09/050988, filed Sep. 1, 2009, which claims benefit under 35 U.S.C. 119(e) of U.S. Provisional Patent Application Ser. No. 61/136,369, filed Sep. 2, 2008 and claims benefit to Swedish Application No. 0801887-1, filed Sep. 1, 2008, the entire contents which are incorporated herein by reference.

FIELD OF INVENTION

The present invention relates to derivatives of 5-aminolevulinic acid (5ALA) and in particular to derivatives comprising a hydrolysable group at position $C_4$, for use as medicaments. In particular, the medicaments are used as photosensitizing agents in medical applications such as photochemotherapy and diagnosis of disorders or abnormalities of the body.

Moreover, the invention relates to novel derivatives of 5-aminolevulinic acid (5ALA) as such, and in particular to novel derivatives comprising a hydrolysable group at position $C_4$. Pharmaceutical compositions comprising the above derivatives also form part of the invention.

BACKGROUND OF THE INVENTION

Photochemotherapy, or photodynamic therapy (PDT) as it is also known, is a technique for the treatment of various abnormalities or disorders of the skin—or other epithelial organs or mucosa, especially cancers or pre-cancerous lesions, as well as certain non-malignant lesions for example skin complaints such as psoriasis. Photochemotherapy involves the application of photosensitizing (photochemotherapeutic) agents to the affected area of the body, followed by exposure to photoactivating light in order to activate the photosensitizing agents and convert them into cytotoxic form, whereby the affected cells are killed or their proliferative potential diminished.

A range of photosensitizing agents are known, including notably the psoralens, the porphyrins, the chlorins and the phthalocyanins. Such drugs become toxic when exposed to light.

Photosensitizing drugs may exert their effects by a variety of mechanisms, directly or indirectly. Thus for example, certain photosensitizers become directly toxic when activated by light, whereas others act to generate toxic species, e.g. oxidizing agents such as singlet oxygen or other oxygen-derived free radicals, which are extremely destructive to cellular material and biomolecules such as lipids, proteins and nucleic acids. Psoralens are an example of directly acting photosensitizers; upon exposure to light they form adducts and crosslinks between the two strands of DNA molecules, thereby inhibiting DNA synthesis. The unfortunate drawback of this therapy is that unwanted mutagenic and carcinogenic side effects may occur.

This disadvantage may be avoided by selecting photosensitizers with an alternative, indirect mode of action. For example porphyrins, which act indirectly by generation of toxic oxygen species, have no mutagenic side effects and represent more favourable candidates for photochemotherapy. Porphyrins are naturally occurring tetrapyrroles that are precursors in the synthesis of heme. In particular, heme is produced when iron ($Fe^{3+}$) is incorporated in protoporphyrin IX (PpIX) by the action of the enzyme ferrochelatase. PpIX is an extremely potent photosensitizer, whereas heme has no photosensitizing effect.

One such porphyrin-based drug, Photofrin, has been approved as a photosensitizer in the therapy of certain cancers. A considerable disadvantage is that since it must be administered parenterally, generally intravenously, it can cause photosensitization of the skin which may last for several weeks following injection. Photofrin consists of large oligomers of porphyrin and it does not readily penetrate the skin when applied topically. Similar problems exist with other porphyrin-based photosensitizers such as Foscan (temoporfin) or the so-called "hematoporphyrin derivative" (Hpd) which have also been reported for use in cancer photochemotherapy. Hpd is a complex mixture obtained by treating haematoporphyrin with acetic and sulphuric acids, after which the acetylated product is dissolved with alkali. Foscan is a tetrapyrrole derivative with four meta-phenol groups attached, that after intravenous injection leaves the patient hypersensitized up to 3 weeks due to the very slow clearance rate from the body.

To overcome these problems, precursors of PpIX have been investigated for photochemotherapeutic potential. In particular the PpIX precursor 5-aminolevulinic acid (5ALA) has been investigated as a photochemotherapeutic agent for certain skin cancers.

Photodynamic therapy based on topical application of 5-aminolevulinic acid (5ALA) or a derivative thereof, for the treatment of small solid tumors is based on using the body's own biosynthetic route to form the endogenous chromophore protoporfyrin IX (PpIX) [1,2].

In Photodynamic diagnosis (PDD), the strong fluorescence of the chromophore is utilized. Excitation at 400-410 nm yields strong emission in the range 630-640 nm, enabling detection of the tissue in which PpIX is accumulated.

5ALA, which is formed from succinyl CoA and glycine in the first step of heme synthesis, is to a limited extent able to penetrate the skin and lead to a localised build-up of PpIX; since the action of ferrochelatase (the metallating enzyme) is the rate limiting step in heme synthesis, adding an excess amount of exogenous 5ALA (or a derivative thereof) bypasses the natural regulatory mechanisms, and leads to elevated levels of the photosensitizing agent PpIX in the cells, with a notable accumulation in tumorus cells [3,4]. A contributing factor for this is that the final enzyme in heme biosynthesis, ferrochelatase, that incorporates an iron ion into the PpIX ring system, is downregulated in tumor cells, thus leading to enhanced build-up of PpIX levels in cancer cells relative to normal cells.

In PDT, excitation of PpIX at 632 nm is generally used. The singlet excited chromophore undergoes efficient intersystem crossing to the first excited triplet state ($T_1$). In presence of molecular oxygen, the chromophore passes its excitation energy from the $T_1$ state to oxygen, thereby generating highly cytotoxic singlet oxygen. As PpIX is synthesized in the cellular mitocontria, the formed singlet oxygen attacks mitochondrial membranes with high efficiency, thus destroying the cells' capacity to produce energy, whereby the cell in question dies.

By applying 5ALA topically to skin tumors, and then after a few hours exposing the tumors to light, a beneficial photochemotherapeutic effect is obtained (see for example WO91/01727). Since the skin covering basilomas and squamous cell carcinomas is more readily penetrated by 5ALA than healthy skin, and since the concentration of ferrochelatase is low in skin tumors, it has been found that topical application of 5ALA leads to a selectively enhanced production of PpIX in tumors.

Photochemotherapy with 5ALA is not always entirely satisfactory. 5ALA is not able to penetrate all tumors and other tissues with sufficient efficacy to enable treatment of a wide range of tumors or other conditions and 5ALA also tends to be unstable in pharmaceutical formulations. These problems have to a large extent been overcome by the use of straight chain, unsubstituted alkyl 5ALA esters which exhibit improved selectivity for abnormal tissue, non-systemic localization of administered agents, improved uptake and PpIX production, and reduced pain sensation on administration (see WO96/28412).

The concentration of PpIX has been found to reach an optimal therapeutic window 2-4 h after application of 5ALA or derivatives thereof heretofore known and used [2]. The concentration of PpIX decays to normal background levels in 36-48 hours.

Currently, the PDT technique is employed using 5ALA or its methyl or hexyl ester clinically. Also other alkyl esters have been proposed [5].

Alkyl esters of 5ALA, and/or modifications to the amine group, are disclosed in for example U.S. Pat. No. 6,992,107 (family member of WO96/28412).

Recently a class of derivatized 5ALA esters, essentially comprising branched alkyl 5ALA esters and substituted benzyl 5ALA esters were proposed therein, providing advantageous enhanced PDT properties compared to the compounds mentioned above (U.S. Pat. No. 6,992,107; Gierskcky et al).

However, these compounds still exhibit some limitations for use as pharmaceuticals in PDT, e.g. relatively low efficacy of membrane penetration. Such a slow penetration hampers efficient clinical treatment by requiring longer retention times before irradiation, and may negatively influence the acceptance of treatment, both by the patient and the medical profession. Consequently, there exists a need for improved photochemotherapeutic agents.

SUMMARY OF THE INVENTION

The compounds according to the invention comprise a hydrolysable functionality at $C_4$ of 5ALA (the keto group of the parent compound 5ALA) or any of its derivatives modified by substituents at the amino- or carboxylic group, in order to enhance membrane penetration and thus shortening the retention time before irradiation.

Compounds of the invention comprise Formula I $((R_2)_2N-CH_2-C(R_1)-CH_2-CH_2-COOR_2)$ and II $((R_2)_2N-CH_2-C(OR_3)(OR_4)-CH_2-CH_2-COOR_2)$ as outlined in FIG. 1, and pharmaceutically acceptable salts thereof for the use in photodynamic therapy (PDT; also referred to as photochemotherapy) against solid tumors and skin disorders, as antimicrobial, antifungal or antiviral agents, or as a photodiagnostic tool (Photodynamic diagnostics, PDD). Pharmaceutical compositions comprising said compounds, and use of said compounds as a medicament is claimed. Moreover, said compounds for use in the photochemotherapeutic diagnosis and/or treatment of human or animal abnormalities or disorders of the body is also claimed. Use of compounds according to the invention in the manufacture of a medicament for the photochemotherapeutic diagnosis and/or treatment of human or animal abnormalities or disorders of the body is also claimed. Furthermore, methods of diagnosis or photochemotherapy using said compounds and related compounds and compositions, and products and kits comprising said compounds are claimed.

The compounds comprise hydrolysable groups at carbon 4 of 5-aminolevulinic acid, according to FIG. 1. More detailed examples are given in FIG. 2.

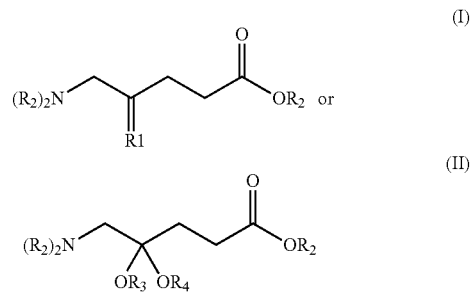

FIG. 1: Molecular Structures in Accordance with the Invention

In the compounds of the invention, for use as a medicament, such as for use in the photochemotherapeutic diagnosis and/or treatment of human or animal abnormalities or disorders of the body, as well as for use in the manufacture of a medicament, $R_1$ may be an oxime, an alkylated oxime, an imine, an alkylated imine, or a hydrazine;
  wherein said alkylated oxime or imine comprises a linear or branched alkyl group of length C1 to C5, such as a linear or branched alkyl group of length C1 to C4;
$R_2$ are each independently
  (a) an unsubstituted or substituted linear or branched alkyl group of chain length $C_{1-7}$,
  (b) an aryl substituted alkyl group, wherein said aryl group is substituted,
  (c) an alkoxy substituted alkyl group, wherein said alkoxy group is substituted by a methoxy group or an alkoxy group substituted with an alkoxy group; or
  (d) an H atom;
  said substituents in (a) and (b) are selected from hydroxy, alkoxy, acyloxy, alkoxycarbonyloxy, amino, aryl, nitro, oxo and fluoro groups.
$R_3$ and $R_4$ are linear or branched alkyl groups of length C1 to C6 constituting a ketal or a cyclic ketal.

There is also claimed novel compounds according to FIG. 1, wherein $R_1$ is an imine or an alkylated imine, said imine or alkylated imine comprising a linear or branched alkyl group of length C1 to C5; such as a linear or branched alkyl group of length C1 to C4.

$R_2$ are each independently
  (a) an unsubstituted or substituted linear or branched alkyl group of chain length $C_{1-7}$;
  (b) an aryl substituted alkyl group, wherein said aryl group is substituted,
  (c) an alkoxy substituted alkyl group, wherein said alkoxy group is substituted by a methoxy group or an alkoxy group substituted with an alkoxy group; or
  (d) an H atom;
  wherein said substituents in (a) and (b) are selected from hydroxy, alkoxy, acyloxy, alkoxycarbonyloxy, amino, aryl, nitro, oxo and fluoro groups.
$R_3$ and $R_4$ are linear or branched alkyl groups of length C1 to C6 constituting a ketal or a cyclic ketal.

In the compounds of the invention, the substituted linear or branched alkyl group of chain length $C_{1-7}$ may e.g. be a linear or branched alkyl chain of length $C_1$ to $C_6$, comprising methyl, ethyl, propyl, butyl, pentyl, and hexyl groups, and iso-forms thereof.

The alkyl group in (a) and (b) above may be interrupted or terminated by one or more —O—, $NR_X$—, —S— or $PR_X$— groups, whereby $R_X$ represents a hydrogen or $C_{1-6}$ alkyl group.

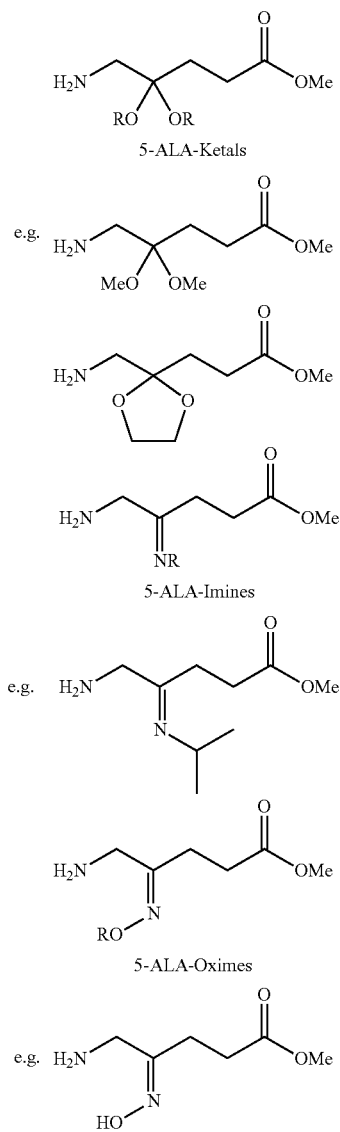

FIG. 2. Examples of the Hydrolysable Molecular Classes Ketals, Imines and Oximes of 5-ALA in for Use as a Medicament in Accordance with the Current Invention.

Entering the cytosol of a cell, the substituted groups will undergo hydrolysis, thereby forming the 5ALA parent compound that is the building block in the biosynthesis of PpIX.

The compounds display very similar dark toxicity (toxicity in cells and tissue not exposed to light), as the parent compound 5ALA, as is apparent from Drawing 1.

Using the spectrum of PpIX as reference (FIG. 2), a comparison between PpIX synthesis by the oxime compound according to the invention with that based on the methyl ester of 5ALA currently in clinical use (MetVix), was made on human living cells using spectrofluorometric measurements. The data shows that 3 h after application, the compound according to the invention generates a higher concentration of PpIX in human cells than does the common 5ALA methyl ester (FIG. 3). The elevated levels of PpIX are retained for at least 6 h after application, as seen in FIG. 4.

The oxime according to the invention is capable of producing PpIX, an efficient photosensitizer that after irradiation by visible light at 632 nm causes cell death as clearly shown in ref. [2].

SHORT DESCRIPTION OF THE DRAWINGS

FIG. 1 shows dose-toxicity in absence of light, obtained using the Promega CytoTox-Glo Cytotoxicity Assay. Diamonds: 5ALA; Squares, dashed: 5ALA oxime.

Figure 4:
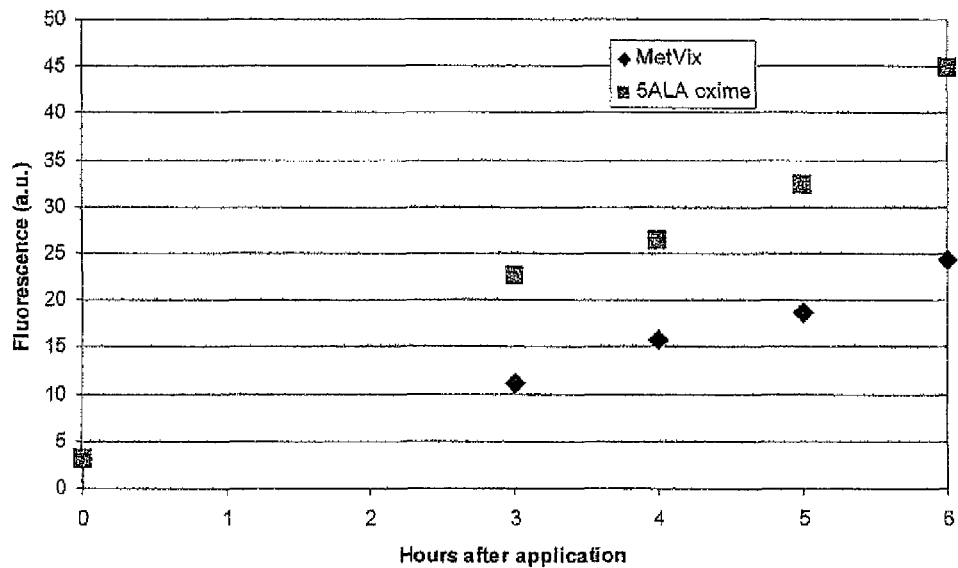

FIG. 4 shows the synthesis of chromophore PpIX in human cells as a function of time after application, measured as fluorescence at 632 nm. Diamonds=5ALA methyl ester (MetVix); Squares=5ALA oxime 20% w/w in Essex™ cream.

DETAILED DESCRIPTION OF THE INVENTION

The present invention according to a first aspect provides derivatives of 5-aminolevulinic acid (5ALA) and in particular derivatives comprising a hydrolysable group at position $C_4$, as medicaments for use as photosensitizing agents in medical applications such as photochemotherapy and diagnosis of disorders or abnormalities of the body. The compounds according to the invention are useful as medicaments due to their valuable pharmacological properties.

The present invention according to a second aspect also provides novel derivatives of 5-aminolevulinic acid (5ALA) having a hydrolysable group at position $C_4$.

The compounds of the invention possess improved properties in terms of enhanced membrane penetration and/or conversion to PpIX, thus enabling the provision of photochemotherapeutic agents which are better pharmaceuticals, i.e. that have an enhanced photochemotherapeutic effect over pharmaceuticals and compounds described in the prior art.

The invention according to the first aspect provides compounds of Formula (I) $((R_2)_2N$—$CH_2$—$C(R_1)$—$CH_2$—$CH_2$—$COOR_2)$ or (II) $((R_2)_2N$—$CH_2$—$C(OR_3)(OR_4)$—$CH_2$—$CH_2$—$COOR_2)$ and salts thereof, for use as a medicament, wherein $R_1$ may be an oxime, an alkylated oxime, an imine, an alkylated imine, or a hydrazine;

said alkylated oxime or imine comprises a linear or branched alkyl group of length C1 to C5;

$R_2$ are each independently (a) an unsubstituted or substituted linear or branched alkyl group of chain length $C_{1-7}$;

(b) an aryl substituted alkyl group, wherein said aryl group is substituted, or (c) an alkoxy substituted alkyl group, wherein said alkoxy group is substituted by a methoxy group or an alkoxy group substituted with an alkoxy group; or (d) an H atom;

said substituents in (a) and (b) are selected from hydroxy, alkoxy, acyloxy, alkoxycarbonyloxy, amino, aryl, nitro, oxo and fluoro groups.

The invention according to the second aspect provides novel compounds of Formula (I) $((R_2)_2N—CH_2—C(R_1)—CH_2—CH_2—COOR_2)$ or (II) $((R_2)_2N—CH_2—C(OR_3)(OR_4)—CH_2—CH_2—COOR_2)$ and salts thereof, wherein $R_1$ may be an imine, an alkylated imine, said imine or alkylated imine comprising a linear or branched alkyl group of length C1 to C5;

$R_2$ are each independently (a) an unsubstituted or substituted linear or branched alkyl group of chain length $C_{1-7}$;

(b) an aryl substituted alkyl group, wherein said aryl group is substituted, or (c) an alkoxy substituted alkyl group, wherein said alkoxy group is substituted by a methoxy group or an alkoxy group substituted with an alkoxy group; or (d) an H atom;

said substituents in (a) and (b) are selected from hydroxy, alkoxy, acyloxy, alkoxycarbonyloxy, amino, aryl, nitro, oxo and fluoro groups.

In relation to the first and second aspects of the invention, $R_3$ and $R_4$ are linear or branched alkyl groups of length C1 to C6 constituting a ketal or a cyclic ketal.

$R_3$ and $R_4$, respectively, are bound to an oxygen, and together with said oxygen and the coals bound thereto constitute a ketal or a cyclic ketal.

According to one embodiment of the first aspect of the invention, the $C_{1-7}$ alkyl group in (a) is a linear or branched alkyl chain of length $C_1$ to $C_6$, comprising methyl, ethyl, propyl, butyl, pentyl and/or hexyl groups, and their iso-forms.

According to another embodiment of the invention, the compound may in the alkyl group in (a) or (b) be interrupted or terminated by one or more —O—, $NR_X$—, —S— or $PR_X$— groups, whereby $R_X$ represents a hydrogen or $C_{1-6}$ alkyl group.

As used herein, the term "alkyl", unless stated otherwise, includes any long or short chain, cyclic, straight-chained or branched aliphatic saturated or unsaturated hydrocarbon group. The unsaturated alkyl groups may be mono- or poly-unsaturated and comprise both alkenyl and alkynyl group. Unless stated otherwise, such groups may contain up to 7 atoms. Alkyl groups containing up to 6, carbon atoms are preferred.

The substituted alkyl $R_2$ groups may be mono or poly-substituted. Suitable $R_2$ groups comprise for example alkoxyalkyl, hydroxyalkoxyalkyl, polyhydroxyalkyl, hydroxy poly alkyleneoxyalkyl and the like.

The branched alkyl group $R_2$ may be a $C_{5-8}$ straight chain alkyl group which is branched by substitution with one or more optionally substituted $C_{1-6}$ alkyl groups, thus forming for example a $C_{6-9}$ alkyl group. Especially preferably the substituents on the $R_2$ group are aryl or alkoxy which may themselves be substituted.

The term "acyl" as used herein includes both carboxylate and carbonate groups, thus, acyloxy substituted alkyl groups may include for example alkylcarbonyloxy alkyl. In such groups any alkylene moieties preferably have carbon atom contents as defined for alkyl groups below.

Exemplary aryl groups include phenyl and monocyclic 5-7 membered heteroaromatics (unless stated otherwise), especially phenyl and such groups may themselves optionally be substituted.

Representative substituted alkyl groups $R_2$ include acylalkyl, alkoxymethyl, alkoxyethyl and alkoxypropyl groups or acyloxymethyl, acyloxyethyl and acyloxypropyl group, e.g., pivaloyloxymethyl.

The hydrolysable moiety at $C_4$ may be in the form of an oxime, a ketal, an imine, or any other hydrolysable functional group.

Upon addition of a compound according to the present invention to living cells (i.e. human or animal tissue), the $C_4$ substituent hydrolyses and the resulting 5ALA undergoes biosynthesis to the naturally occurring chromophore protoporphyrin IX (PpIX).

According to an exemplary embodiment of the invention, the, compounds may be in the form of pharmaceutically acceptable salts. Such salts may be hydrophilic acid addition salts with physiologically acceptable organic or inorganic acids. Suitable acids comprise for example hydrochloric, hydrobromic, sulphuric, phosphoric, acetic, lactic, citric, tartaric, succinic, maleic, fumaric and ascorbic acids. Hydrophobic salts may also conveniently be produced by for example precipitation. Appropriate such salts comprise for example acetate, bromide, chloride, citrate, hydrochloride, maleate, mesylate, nitrate, phosphate, sulphate, tartrate, oleate, stearate, tosylate, calcium, meglumine, potassium and sodium salts. Procedures for salt formation are known in the art. Moreover, pharmaceutically acceptable solvents and salts, as well as physiologically acceptable acids, are known to the person skilled in the art, and may be found in e.g. the Pharmacopeia.

A third aspect of the present invention provides a pharmaceutical composition comprising a compound, or a pharmaceutically acceptable salt thereof, as described hereinbefore, together with at least one pharmaceutical carrier or excipient.

In a first embodiment of this third aspect of the invention, the pharmaceutical compound is present in an amount in the range of 0.01 to 90% by weight.

In a second embodiment of said aspect, the pharmaceutical compound is present in an amount in the range of 0.05 to 50% by weight.

In a third embodiment of said aspect, the pharmaceutical compound is present in an amount in the range of 1 to 20% by weight.

The compositions according to the present invention may be provided in a form suitable for systemic, intratumoral, intradermal, subcutaneous, intraperitoneal, intracavitary, intraocular or intravenous injection, or topical administration.

The concentration of the compounds as described hereinbefore in the compositions, depends upon the nature of the compound, the composition, mode of administration, the condition to be treated and the patient and may be varied or adjusted according to choice. Generally however, concentration ranges of 0.01 to 90% (w/w) are suitable. For therapeutic applications concentration ranges of 0.1 to 50% have been found to be suitable, e.g. 0.2 to 30% (w/w). Lower doses may be used when derivatives are prepared which are highly lipophilic, e.g. a concentration range of 0.01 to 10%, e.g. 0.02 to 1% (w/w).

The compositions of the invention may be formulated in conventional manner with one or more physiologically acceptable carriers or excipients, according to techniques well known in the art. Where appropriate, compounds or compositions according to the invention are sterilized, e.g. by γ-irradiation, autoclaving or heat sterilization, before or after the addition of a carrier or excipient, where applicable, to provide sterile formulations.

Compositions may be administered topically, orally or systemically. Topical compositions are preferred, and may include conventional gels, creams, ointments, sprays, lotions, salves, sticks, soaps, powders, pessaries, aerosols, drops, solutions, patches, direct injection and any of the other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant. The compound may in a form for topical administration be provided in solid form, to be reconstituted with a solvent before or in conjunction with treatment. Providing the compound in solid form may improve its storage stability.

Alternatively, the compositions may be provided in a form adapted for oral or parenteral administration, for example by intradermal, subcutaneous, intraperitoneal, intratumoral, intracavitary, intraocular or intravenous injection. Alternative pharmaceutical forms thus include plain or coated tablets, capsules, suspensions and solutions containing the compound or composition according to the invention, optionally together with one or more inert conventional carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

The compositions of the invention may additionally include lubricating agents, wetting agents, emulsifying agents, suspending agents, preserving agents, sweetening agents, flavouring agents, adsorption enhancers, e.g. surface penetrating agents as mentioned below, and the like. The compositions of the invention may be formulated so as to provide quick, sustained or delayed release of the compound after administration to the patient by employing procedures well known in the art. Solubilizing and/or stabilizing agents may also be used, e.g. cyclodextrins (CD) $\alpha$, $\beta$, $\gamma$ and HP-$\beta$ cyclodextrin. Compositions may be in any appropriate dosage form, for example as an emulsion or in liposomes, niosomes, microspheres, nanoparticles or the like. The compound of the invention may then be absorbed to, incorporated in or bound to these forms.

Topical administration to inaccessible sites may be achieved by techniques known in the art, e.g. by the use of catheters or other appropriate drug delivery systems.

The pharmaceutical compositions according to the invention, as described herein, are suitable for use as a medicament, e.g. in photochemotherapy or diagnosis of disorders or abnormalities of the body. One aspect of the invention hence relates to the use of a substance according to the present invention in the manufacture of a medicament for the photochemotherapeutic diagnosis and/or treatment of human or animal abnormalities or disorders of the body.

The human or animal abnormalities and disorders which may be treated according to the present invention include any malignant, pre-malignant and non-malignant abnormalities or disorders responsive to photochemotherapy, eg., tumors or other growths, skin disorders such as psoriasis or actinic keratoses and acne, skin abrasions, age related macular degeneration, and other diseases or infections, eg. bacterial, viral or fungal infections, for example Herpes virus infections. The invention is particularly suited to the treatment of diseases, disorders or abnormalities where discrete lesions are formed to which the compositions may be directly applied (lesions is used here in a broad sense to include tumours and the like).

The term "disorders och abnormalities" is used herein as also comprising medical imbalances, diseases, and syndromes as well as bacterial and viral infections.

The internal and external body surfaces, herein also referred to as merely "tissue", which may be treated in accordance with the invention include the skin and all other epithelial and serosal surfaces, including for example mucosa, the linings of organs eg. the respiratory, gastro-intestinal and genitourinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue eg. brain cavities following the excision of tumours such as gliomas.

Exemplary surfaces may thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumors in solid tissues that can be made accessible to photoactivating light e.g. either directly, at time of surgery, or via an optical fibre inserted through a needle.

"Tissue" and "body fluid" are used herein as meaning any human or animal tissue and body fluid that may be treated, wholly or in part, or otherwise altered or affected by way of photochemotherapeutics.

Following administration to the surface, the area treated is exposed to light to achieve the photochemotherapeutic effect. The length of time following administration, at which the light exposure takes place will depend on the nature of the composition, the condition to be treated and the form of administration. This can generally be in the order of 0.5 to 48 hours, e.g. 1 to 10 hours.

The irradiation will in general be applied at a dose level of 40 to 200 Joules/cm$^2$, for example at 100 Joules/cm$^2$.

The wavelength of light used for irradiation may be selected to achieve a more efficacious photochemotherapeutic effect. Conventionally, when porphyrins are used in photochemotherapy they are irradiated with light at about the absorption maximum of the porphyrin. Thus, for example in the case of the prior art use of 5ALA in photochemotherapy of skin cancer, wavelengths in the region 350-640 nm, preferably 610-635 nm were employed. However, by selecting a broad range of wavelengths for irradiation, extending beyond the absorption maximum of the porphyrin, the photosensitizing effect may be enhanced. Whilst not wishing to be bound by theory, this is thought to be due to the fact that when PpIX, and other porphyrins, are exposed to light having wavelengths within its absorption spectrum, it is degraded into various photo-products including in particular photoprotoporphyrin (PPp). PPp is a chlorin and has a considerable photo-sensitizing effect; its absorption spectrum stretches out to longer wavelengths beyond the wavelengths at which PpIX absorbs ie. up to almost 700 nm (PpIX absorbs almost no light above 650 nm). Thus in conventional photochemotherapy, the wavelengths used do not excite PPp and hence do not obtain the benefit of this additional photosensitizing effect. Irradiation with wavelengths of light in the range 500-700 nm has been found to be particularly effective. It is particularly important to include the wavelengths 630 and 690 nm.

A further aspect of the invention thus provides a method of photochemotherapeutic treatment of disorders or abnormalities of external or internal surfaces of the body, comprising administering to the affected surfaces, a composition as hereinbefore defined, and exposing said surfaces to light, preferably to light in the wavelength region 300-800 nm, for example 500-700 nm.

Methods for irradiation of different areas of the body, eg. by lamps or lasers are well known in the art (see for example Van den Bergh, Chemistry in Britain, May 1986 p. 430-439). For inaccessible regions irradiation may conveniently be achieved using optical fibres.

The compounds of the invention or for use in the invention may be formulated and/or administered with other photosensitizing agents, for example 5ALA or Photofrin™, or with other active components which may enhance the photochemotherapeutic effect. For example, chelating agents may beneficially be included in order to enhance accumulation of PpIX; the chelation of iron by the chelating agents prevents its incorporation into PpIX to form heme by the action of the enzyme ferrochelatase, thereby leading to a build-up of PpIX. The photosensitizing effect is thus enhanced.

Aminopolycarboxylic acid chelating agents are particularly suitable for use in this regard, including any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA and DOTA and well known derivatives/analogues thereof. EDTA is preferred. To achieve the iron-chelating effect, desferrioxamine and other siderophores may also be used, e.g. in conjunction with aminopolycarboxylic acid chelating agents such as EDTA.

The chelating agent may conveniently be used at a concentration of 0.05 to 20% e.g. 0.1 to 10% (w/w).

Alternatively or additionally, inhibitors of ferrochelatase can be utilized in combination with said compounds, which also enhances accumulation of PpIX.

Additionally, it has been found that surface-penetration assisting agents and especially dialkylsuphoxides such as dimethylsulphoxide (DMSO) may have a beneficial effect in enhancing the photochemotherapeutic effect. This is described in detail in WO95/07077.

The surface-penetration assisting agent may be any of the skin-penetration assisting agents described in the pharmaceutical literature e.g. chelators (e.g. EDTA), surfactants (e.g. sodium dodecyl sulphate), non-surfactants, bile salts (e.g. sodium deoxycholate) and fatty acids (e.g. oleic acid). Examples of appropriate surface penetrating assisting agents include HPE-101 (available from Hisamitsu), DMSO and other dialkylsulphoxides, in particular n-decylmethylsulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167-177), and Azone™ (Stoughton et al., Drug Dpv. Ind. Pharm. 1983, 9: 725-744), or mixtures thereof.

DMSO is however preferred due to its anti-histamine and anti-inflammatory activities and its stimulatory effect on the activity of the enzymes ALA-synthase and ALA-dehydrogenase (the enzymes which, respectively, form and condense ALA to porphobilinogen) thereby enhancing the formation of the active form, PpIX.

The surface penetration agent may conveniently be provided in a concentration range of 0.2 to 50% (w/w), e.g. about 10% (w/w).

The compositions of the invention or use thereof according to the invention may additionally be formulated and/or administered with other agents, to improve the efficacy of PDT. Furthermore, when treating tumours for example; angiogenesis inhibitors (anti-angiogenic drugs) which have been found to be useful for treating tumours (O'Reilly et al., Nature Medicine, 2, p 689-692, 1996; Yamamoto et al., Anticancer Research, 14, p 1-4, 1994; and Brooks et al., J. Clin. Invest., 96, p 1815-1822, 1995) may be used together with compositions of the invention in PDT to further damage the vascular system of the tumour. Angiogenesis inhibitors which may be used include TNP-470 (AGM-1470, a synthetic analogue of a fungal secretion product called fumagillin; Takeda Chemical Industries Ltd., Osaka, Japan), angiostatin (Surgical Research Lab at Children's Hospital Medical Center of Harvard Medical School) and integrin $\alpha_v\beta_3$ antagonists (e.g. monoclonal antibody to integrin $\alpha_v\beta_3$, The Scripps Research Institute, LaJolla, Calif.).

Alternatively, or additionally, immunotherapy agents (e.g. antibodies or effectors such as macrophage activating factor) or chemotherapy agents may be used to improve PDT according to the invention. Administration of these supplementary agents should be performed in terms of route, concentration and formulation, according to known methods for using these agents. These additional agents may be administered before, after or during PDT, depending on their function. For example, angiogenesis inhibitors may be added 5 to 10 days after PDT to prevent tumor re-growth.

Other anti-cancer agents may similarly be used in combination with a composition of the invention, either as part of the formulation or as a separate treatment to be administered simultaneously, separately or sequentially.

Glucose has also been found to assist PDT when applied either topically or systemically. It appears that administration of glucose results in a lowering of pH which increase the hydrophobic properties of protoporphyrins, e.g. 5ALA, such that they can penetrate cells more easily. When topical administration is contemplated, conveniently the formulation, e.g. a cream, may contain 0.01% to 10% glucose (w/w).

According to the condition being treated, and the nature of the composition, the compounds for use in the invention may be co-administered with such other optional agents, for example in a single composition or they may be administered sequentially or separately. Indeed, in many cases a particularly beneficial photochemotherapeutic effect may be obtained by pre-treatment with the surface-penetration assisting agent in a separate step, prior to administration of the compounds for use in accordance with the invention.

The pharmaceutical composition may in addition to the compound of the invention additionally comprise one or several compounds chosen from: chelating agents, inhibitors of ferrochelatase, immunotherapeutic agents, angiogenesis inhibitors, surface penetration assisting agents, photosensitizing agents, glucose, anti-cancer agents, and anaesthetic or analgesic agents. The compounds belonging to the above group are known to the person skilled in the art.

According to a fourth aspect of the invention, there is provided a method of diagnosis or photochemotherapeutic treatment of disorders or abnormalities of the body, comprising administering to an affected tissue, a composition according to the present invention, and exposing said tissue to light.

In some situations a pre-treatment with a surface-penetration assisting agent, followed by administration of the photochemotherapeutic agent in conjunction with the surface-penetration assisting agent may be beneficial. When a surface-penetration assisting agent is used in pre-treatment this may be used at high concentrations, e.g. up to 100% (w/w). If such a pre-treatment step is employed, the photochemotherapeutic agent may subsequently be administered up to several hours following the pre-treatment eg. at an interval of 5-60 minutes following pre-treatment. In one embodiment, the method of the invention thus additionally comprises prior to the treatment a pre-treatment step with a surface penetration assisting agent.

The invention thus provides a compound or a pharmaceutically acceptable salt thereof, in accordance with the invention, together with at least one surface-penetration assisting agent, and optionally one or more chelating agents as a combined preparation for simultaneous, separate or sequential use in treating disorders or abnormalities of external or internal surfaces of the body which are responsive to photochemotherapy.

According to one embodiment, the method of the invention additionally comprises treatment with an anaesthetic agent. Anaesthetics used with the current invention are primarily local anaesthetics, such as prilocaine and lidocaine.

It will be appreciated that the method of therapy using compounds in accordance with the invention as described herein inevitably involves the cell fluorescence of the disorder or abnormality to be treated. Whilst the intensity of this fluorescence may be used to eliminate abnormal cells, the localization of the fluorescence may also be used to visualize the size, extent and localization of the abnormality or disorder.

The abnormality or disorder thus identified or confirmed at the site of investigation may then be treated through alternative therapeutic techniques e.g. surgical or chemical treatment, or by the method of therapy of the invention by continued build-up of fluorescence or through further application of compounds of the invention at the appropriate site. It will be appreciated that diagnostic techniques may require lower levels of fluorescence for visualization than used in therapeutic treatments. Thus, generally, concentration ranges of 0.2 to 30% e.g. 1-5% (w/w) are suitable. Sites, methods and modes of administration have been considered before herein with regard to the therapeutic uses and are applicable also to the diagnostic uses described here.

Accordingly, according to a fifth aspect of the invention, there is provided a method of in vivo diagnosis or photochemotherapeutic treatment of disorders or abnormalities of human or animal tissue, comprising: a) administering to said tissue, a composition comprising a compound according to the present invention, or a pharmaceutically acceptable salt thereof, and at least one pharmaceutical carrier or excipient; and b) exposing said tissue to light in the wavelength region of 300-800 nm.

The compounds of the invention may also be used for in vitro diagnostic techniques, for example for examination of the cells contained in body fluids.

Accordingly, in a sixth aspect of the invention, there is provided an assay for in vitro diagnosis of human or animal abnormalities or disorders, comprising: i) providing a sample of body fluid or tissue; ii) admixing said body fluid or tissue with a composition comprising a compound in accordance with the invention or a pharmaceutically acceptable salt thereof, and at least one pharmaceutical carrier or excipient compound; iii) exposing said mixture to light, iv) ascertaining the level of fluorescence, and v) comparing the level of fluorescence to control levels.

The higher fluorescence associated with non-normal tissue may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, spinal fluid etc. Tissue samples or preparations may also be evaluated, for example biopsy tissue or bone marrow samples. The present invention thus extends to the use of compounds of the invention, or salts thereof for diagnosis according to the aforementioned methods for photochemotherapy, and products and kits for performing said diagnosis.

In a final, seventh aspect of the invention, there is provided a kit comprising a compound according to the invention in solid form, a solvent, and optionally additionally comprising one or more anaesthetic agents.

The person skilled in the art realizes that the examples and embodiments provided herein are merely intended to disclose the spirit and scope of the current invention in accordance with the appended claims, and shall not be seen as any limitation whatsoever.

EXAMPLES

Synthesis of said compounds has been conducted according to two routes. The compounds used as starting materials herein are known from the literature, and in many cases commercially available, or may be obtained using methods known to the person skilled in the art. 5ALA, for example, is available from Sigma Aldrich.

A. Synthesis of 5-ALA Oxime Acid or Corresponding Methylated Compound from 5-Aminolevulinic Acid or Methyl-Aminolevulinic Acid.

To a mixture of 5-ALA acid (or methyl-ALA) (3 g, 18 mmol) in EtOH (12 ml) at room temperature was added in one portion a clear solution of hydroxylamine hydrochloride (2.16 g, 31 mmol) and NaOAc (2.16 g, 26 mmol) in $H_2O$ (9.6 ml). The resulting mixture gave after a couple of minutes a clear solution and was stirred at reflux for 1.5 hours after which time the reaction was completed according to $^1H$ NMR.

After the clear slightly yellow solution had cooled to room temperature, EtOH was removed from the reaction under reduced pressure. To the aqueous phase was then added successively and stirred several portions of $CH_3CN$ (50 ml, 60 ml, 70 ml). After each step excess $CH_3CN$ phase was removed.

The mixture was filtered giving 5-ALA oxime as a white solid (2.6 g, 110%) where the contamination is most likely organics or solvents.

$^1H$ NMR ($D_2O$, 400 MHz): 3.7 (s, 2H), 2.5-2.6 (m, 4H)

$^{13}C$ NMR ($D_2O$, 400 MHz): 117.91 ($CO_2H$), 153.25 (C=N—OH), 40.83 ($CH_2$), 36.49 ($CH_2$), 30.78 ($CH_2$), 30.02 ($CH_2$), 22.37 ($CH_2$), 28.36 ($CH_2$)

$[M+H]^+$=147.

B. Synthesis of 5ALA Ketals and Imines Using 3-Hydroxypiperidine HU as Starting Material.

Figure 1:
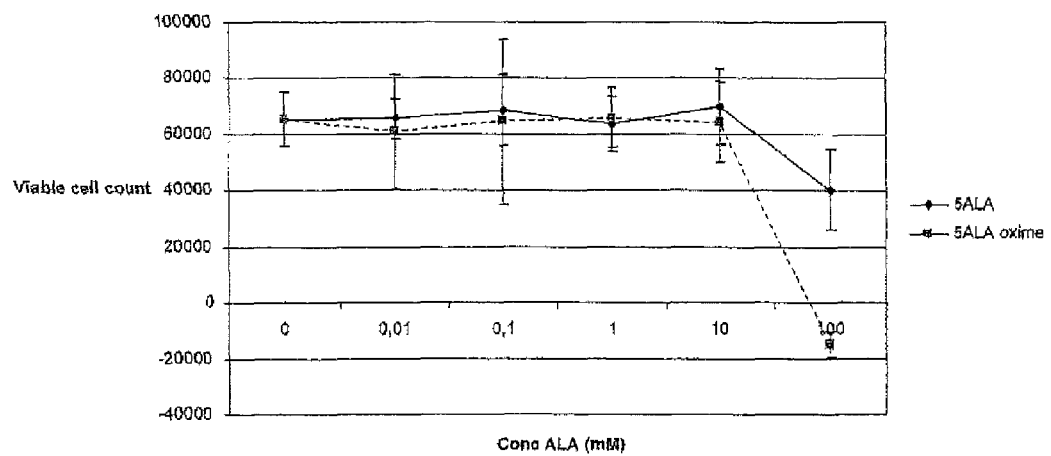
Figure 2:
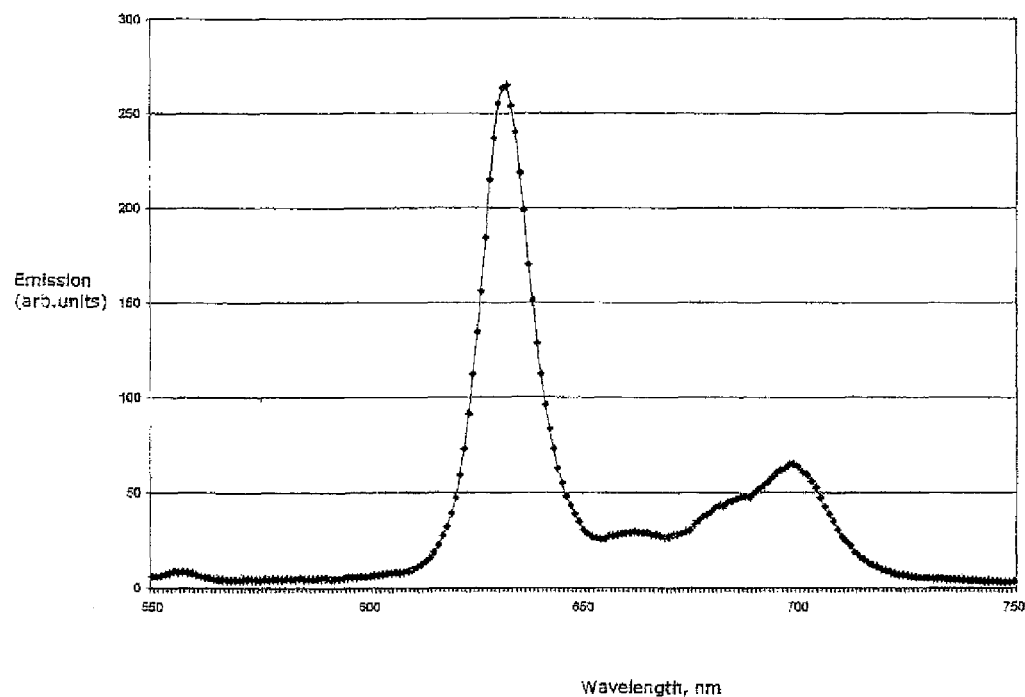
FIG. 2 shows the experimental absorption spectrum of the chromophore Protoporphyrin IX (PpIX).
Figure 3:
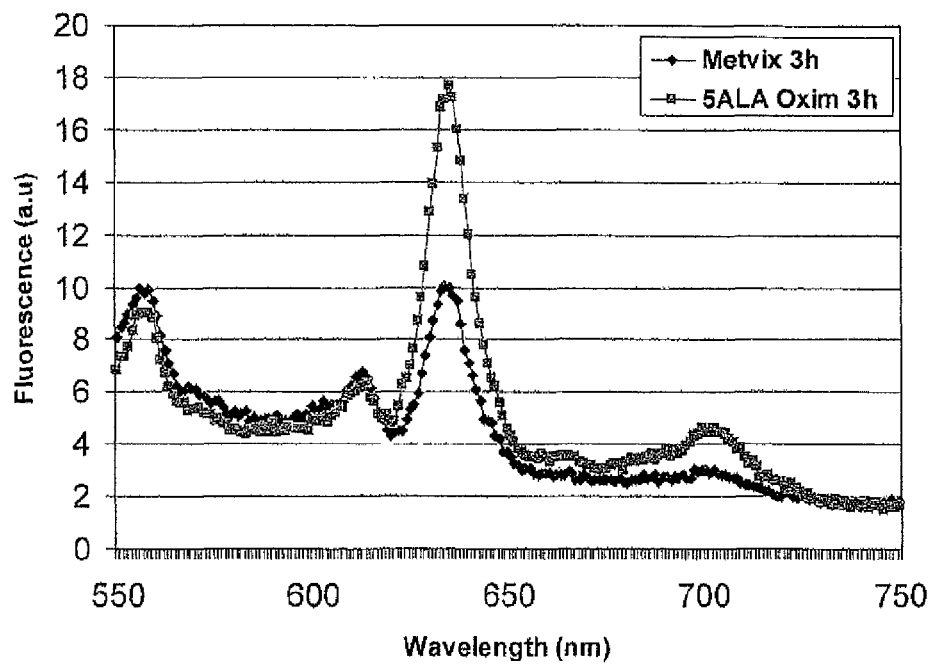
FIG. 3 shows the production of PpIX in human cells by (Diamonds) 5-ALA methyl ester (MetVix) and (Squares) 5-ALA oxime 20% (w/w), using the commercially available Essex™ cream, recorded 3 h after application.

Synthesis of ketals and oximes can be undertaken as outlined in FIG. 3.

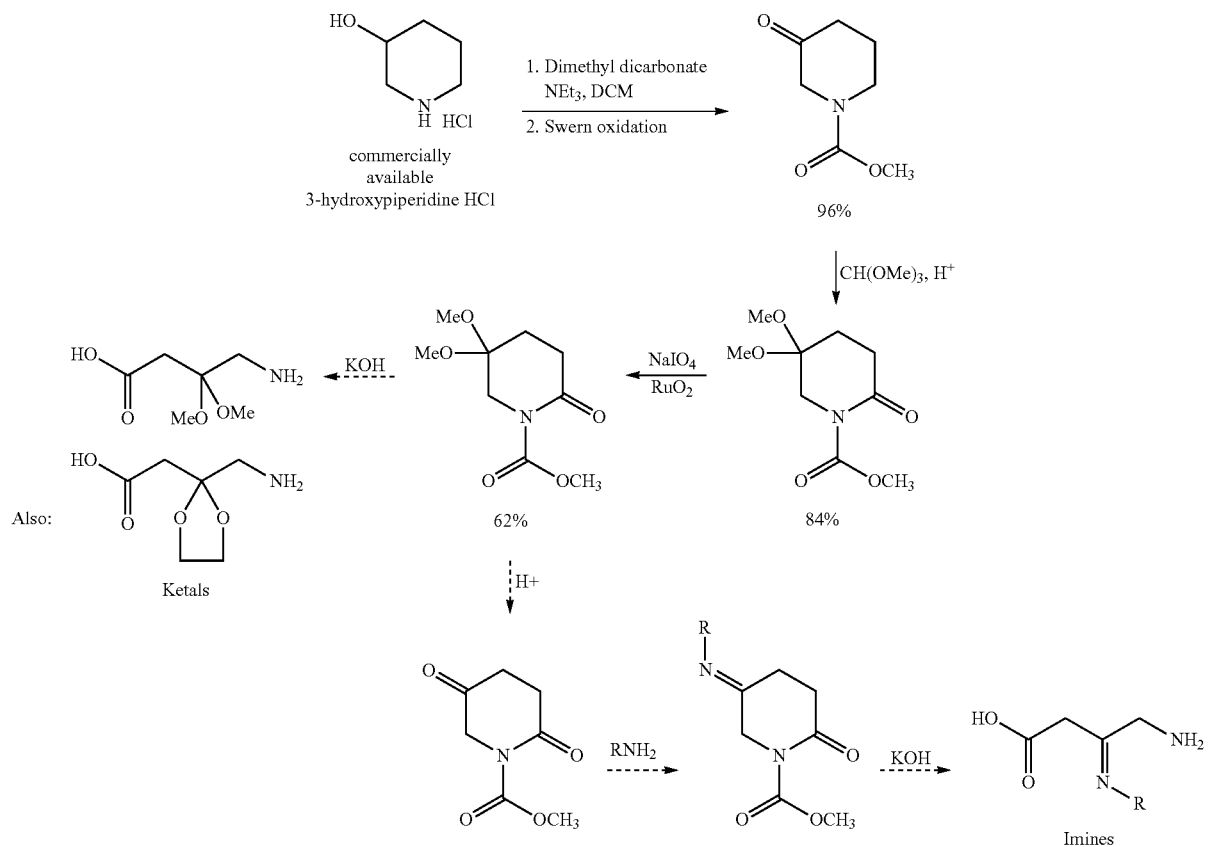

FIG. 3. General Synthetic Route to Hydrolysable 5ALA Derivatives

A detailed outline of synthesis of one ketal derivative based on the above description is given as follows below.

3.1.1 5-δ-Amino Levulinic Acid Ketal Derivative (5-ALA)

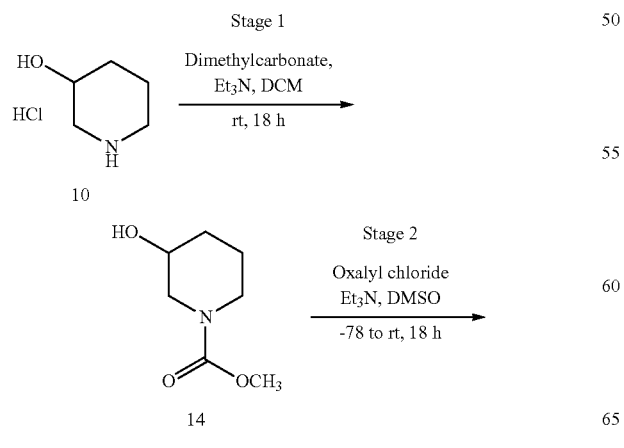

-continued

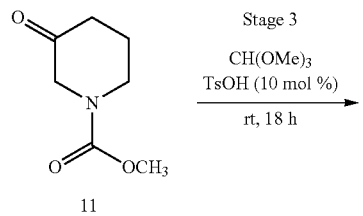

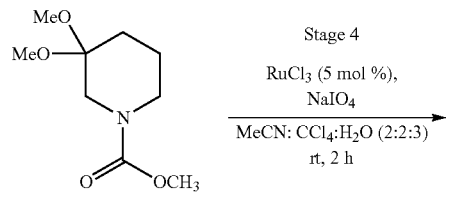

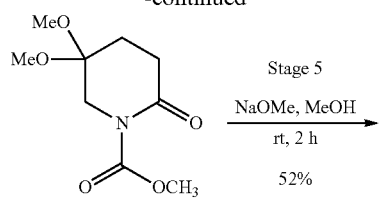

Stage 5
NaOMe, MeOH
rt, 2 h
52%

16
25%~60% purity

4.2.1 Stage 1; Synthesis of 3-Hydroxy-Piperidine-1-Carboxylic Acid Methyl Ester 14 (LBN 557-077)

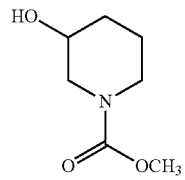

14

To a mixture of 3-hydroxypiperidine HCL 10 (15.0 g, 0.11 mol, 1.0 eq) in DCM (225 ml, 15 vol) was added $Et_3N$ (16.6 g, 0.16 mol, 1.5 eq). To the suspension at 0° C. was added dimethyldicarbonate (14.6 g, 0.11 mol, 1.0 eq) in DCM (30 ml, 2.0 vol cf sm) over 20 min ($T_{max}$<7° C.). The mixture was allowed to warm to rt and stirred overnight for 18 h. After this time a $^1$H NMR spectrum ($CDCl_3$) of the crude material showed the reaction mixture to contain 20% sm 10. Further dimethyldicarbonate (2.19 g, 16.3 mmol, 0.15 eq) was added in one portion. After a further 2 h at it the reaction was seen to be complete by $^1$H NMR spectroscopy. $H_2O$ (75 ml, 5.0 vol) was added and the layers separated. The organic layer washed with 10% w/v citric acid (75 ml, 5.0 vol) and $H_2O$ (75 ml, 5.0 vol). The layers were separated and the organic layer dried ($MgSO_4$) filtered and concentrated under reduced pressure providing the title compound 14 557-078-4 (10.0 g, 58% yield) as a clear oil. The combined aq layers were then saturated with NaCl and extracted with DCM (2×100 ml, 7.0 vol). The combined organic layers were washed with brine (100 ml), dried ($MgSO_4$), filtered and concentrated under reduced pressure. After drying to constant weight provided further 14 557-078-6 (7.00 g, 40% yield).

$^1$H NMR ($CDCl_3$, 400 MHz): δ 3.70-3.56 (m, 6H), 3.20-3.10 (m, 2H), 2.80-2.20 (m, 1H), 1.90-1.80 (m, 2H), 1.50-1.40 (m, 2H)

4.2.2 Stage 2; Synthesis of 3-Oxo-Piperidine-1-Carboxylic Acid Methyl Ester 11 (LBN 557-079)

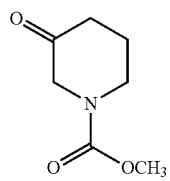

11

To DCM (300 ml, 30 vol) at −60° C. was added oxalyl chloride (9.58 g, 0.08 mol, 1.2 eq), followed by the dropwise addition of DMSO (9.83 g, 0.13 mol, 2.0 eq) over 5 min. To this solution was added 14 (10.0 g, 0.06 mol, 1.0 eq) in DCM (150 ml, 15 vol) over 15 min at −78° C. The solution was allowed to stir at −78° C. for 5 min then $Et_3N$ (25.5 g, 0.25 mol, 4.0 eq) was added over 15 min and the reaction then allowed to warm to rt and stirred overnight. After this time the reaction was seen to be complete by $^1$H NMR spectroscopy. The organic layer was then washed with sat. $NH_4Cl$ (2×150 ml, 15 vol), sat. $NaHCO_3$ (150 ml, 15 vol) and brine (150 ml, 15 vol). The organic layer was dried ($MgSO_4$), filtered and the solvent concentrated under reduced pressure. Toluene (30 ml, 3.0 vol) was added and the solvent was removed under reduced pressure. After drying to constant weight the title compound 11 557-080-4 (8.73 g, 88% yield) was obtained as a clear oil. This material was of sufficient purity to use in the next step.

$^1$H NMR (DMSO-$d_6$, 400 MHz): δ 1.61-1.68 (m, 2H), 2.14 (t, 2H, J=7.0 Hz), 3.27 (t, 2H, J=6.0 Hz), 3.35 (s, 3H), 3.66 (s, 2H)

4.2.3 Stage 3; Synthesis of 3,3-Dimethoxy-Piperidine-1-Carboxylic Acid Methyl Ester 15 (LBN 557-081)

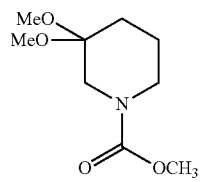

15

To a solution of 11 (11.9 g, 76 mmol, 1 eq) in trimethylorthoformate (80 ml, 6.7 vol) at rt was added p-TsOH (50 mg, cat) and the solution stirred at rt 18 hours. After this time the reaction was found to only contain sm by $^1$H NMR spectroscopy so further p-TsOH (150 mg, 1.00 mmol, 0.1 eq) was added. After a further 3 h at rt the reaction was found to be complete. To the reaction was added aq sat. $NaHCO_3$ (85 ml, 7.0 vol) and DCM (85 ml, 7.0 vol) and the layers separated. The aqueous layer was extracted with DCM (2×120 ml, 10 vol) and the combined organics washed with $H_2O$ (85 ml, 7.0 vol) then dried ($MgSO_4$), filtered and concentrated under

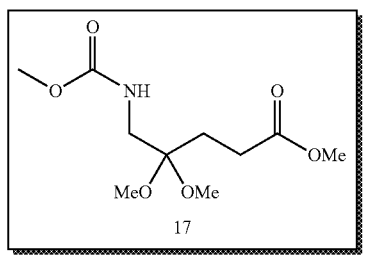

17 reduced pressure. After drying to constant weight the title compound 15 557-081-3 (10.5 g, 78% yield) was obtained as a clear oil. This material was of sufficient purity to use in the next step.

$^1$H NMR (CDCl$_3$, 400 MHz): δ 1.55-1.70 (m, 2H), 1.70-1.81 (m, 2H), 3.22 (s, 6H), 3.45-3.53 (m, 4H), 3.71 (s, 3H)

4.2.4 Stage 4; Synthesis of 5,5-Dimethoxy-2-Oxo-Piperidine-1-Carboxylic Acid Methyl Ester 16 (LBN 603-015)

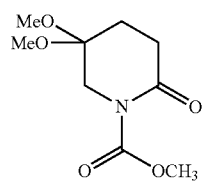

16

To a mixture of NaIO$_4$ (15.8 g, 74 mmol, 5 eq), 15 (3.00 g, 14.8 mmol, 1 eq) in CCl$_4$ (60 ml, 20 vol), MeCN (60 ml, 20 vol) and H$_2$O (90 ml, 30 vol) at rt was added in one portion RuCl$_3$ (153 mg, 0.74 mmol, 0.1 eq) and the mixture stirred at rt for 4 h. After this time further NaIO$_4$ (15.8 g, 74 mmol, 5 eq) was added and the mixture was stirred at rt for 18 h, after which, the reaction was complete. The layers were separated and the aqueous layer extracted with DCM (3×90 ml, 30 vol). The combined organic layers were dried (MgSO$_4$), filtered and concentrated under reduced pressure providing a black oil 603-015-1 containing ~60% 16 by $^1$H NMR spectroscopy. The crude material 603-015-1 was purified by column chromatography eluting with 30% to 50% iPrOAc/heptane. The product containing fractions were combined and provided 16 603-020-5 (634 mg, 20% yield, ~60% purity $^1$H NMR) as a clear oil.

$^1$H NMR (CDCl$_3$, 400 MHz): δ 2.02 (t, 2H, J=6.0 Hz), 2.59 (t, 2H, J=6.0 Hz), 3.25 (s, 6H), 383 (s, 2H), 3.88 (s, 3H)

4.2.5 Stage 5; Synthesis of 4,4-Dimethoxy-5-methoxycarbonylamino-pentanoic acid methyl ester (LBN 603-021)

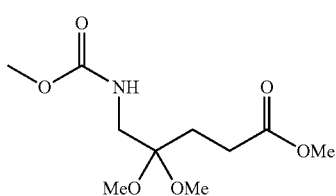

17

To a cooled (0° C.) solution of 16 (635 mg, 2.93 mmol, 1 eq) in anhydrous MeOH (1.3 ml, 2.0 vol) under an atmosphere of nitrogen was added NaOMe (160 mg, 2.93 mmol, 1 eq). After 1 h the reaction was complete by TLC. DCM (10 ml, 17 vol) and H$_2$O (4 ml, 7.0 vol) were added and the layers separated. The aqueous layer was extracted with DCM (3×10 ml) and the combined organics dried (MgSO$_4$), filtered and concentrated under reduced pressure providing a clear oil 603.021-1. The crude material 603-021-1 was purified by column chromatography eluting with 30% iPrOAc/heptane to (1:1) iPrOAc/heptane. The product containing fractions were combined and provided 17 603-022-2 (380 mg, 52% yield, 96% purity $^1$H NMR$_{w/w}$) as a pale yellow solid.

$^1$H NMR (CDCl$_3$, 400 MHz): δ 3.67 (s, 3H), 3.27 (d, 2H, J=6.5 Hz), 3.19 (s, 6H), 2.39 (t, 2H, J=8.5 Hz), 1.93 (t, 2H, J=8.5 Hz)

REFERENCES

[1] *Photodynamic Therapy*; Patrice, T., Ed.; RSC Publishing: 2003, and references therein.
[2] *Photodynamic Therapy with ALA*; Pottier, C., Krammer, B., Stepp, H., Baumgartner, R., Eds.; RSC Publishing: 2006, and references therein.
[3] Navone, N. M., et al. *Medical Science Research* 1988, 16, 61-2.
[4] van Hillegersberg, R., et al. *Gastroenterology* 1992, 103, 647-51.
[5] Pushpan, S. K., et al. *Current Medicinal Chemistry—Anti-Cancer Agents* 2002, 2, 187-207.

The invention claimed is:

1. A method of photochemotherapeutic treatment of a disorder or abnormality of the body, comprising administering to an affected tissue of a subject in need thereof an effective amount of a composition comprising a compound of Formula (I) or (II)

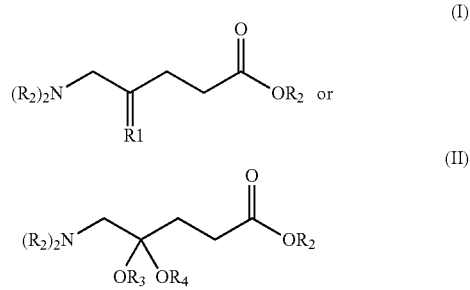

or a pharmaceutically acceptable salt of the compound of Formula (I) or (II), and exposing the affected tissue to light, wherein:
R$_1$ is an oxime, an alkylated oxime, an imine, or a hydrazine; wherein said alkylated oxime imine comprises a linear or branched alkyl group of length C1 to C5;
R$_2$ are each independently:
(a) an unsubstituted or substituted linear or branched alkyl group of chain length C$_{1-7}$,
(b) an aryl substituted alkyl group, wherein said aryl group is substituted,
(c) an alkoxy substituted alkyl group, wherein said alkoxy group is substituted by a methoxy group or an alkoxy group substituted with an alkoxy group, or
(d) an H atom, wherein said substituents in (a) and (b) are selected from the group consisting of hydroxy, alkoxy, acyloxy, alkoxycarbonyloxy, amino, aryl, nitro, oxo and fluoro groups; and
R$_3$ and R$_4$ are independently linear or branched alkyl groups of length C1 to C6 comprising a ketal or a cyclic ketal.

2. The method of claim 1, wherein R$_1$ is an imine.

3. The method of claim 1, wherein the C$_{1-7}$ alkyl group in (a) is a linear or branched alkyl chain of length C$_1$ to C$_7$, selected from the group consisting of methyl, ethyl, propyl, butyl, pentyl, hexyl, and heptyl groups and iso-forms thereof.

4. The method of claim 1, wherein the alkyl group in (a) or (b) is interrupted by one or more —O—, $NR_X$—, —S— or $PR_X$— groups, wherein $R_X$ represents a hydrogen or $C_{1-6}$ alkyl group.

5. The method of claim 1, wherein the pharmaceutically acceptable salt of formula (I) or (II) is selected from the group consisting of hydrochloric, hydrobromic, sulphuric, phosphoric, acetic, lactic, citric, tartaric, succinic, maleic, fumaric, ascorbic acid, acetate, bromide, chloride, citrate, maleate, mesylate, nitrate, phosphate, sulphate, tartrate, oleate, stearate, tosylate, calcium, meglumine, potassium, and sodium salt.

6. The method of claim 1, wherein the composition further comprises at least one pharmaceutically acceptable carrier or excipient.

7. The method of claim 1, wherein the composition further comprises at least one component selected from the group consisting of chelating agents, inhibitors of ferrochelatase, immunotherapeutic agents, angiogenesis inhibitors, surface penetration assisting agents, photosensitizing agents, glucose, anti-cancer agents, and anesthetic or analgesic agents.

8. The method of claim 1, wherein the compound of Formula (I) or (II), or the pharmaceutically acceptable salt of Formula (I) or (II), is present in the composition in an amount in the range of 0.01 to 90% by weight.

9. The method of claim 8, wherein the compound is present in the composition in an amount in the range of 0.05 to 50% by weight.

10. The method of claim 9, wherein the compound is present in the composition in an amount in the range of 1 to 20% by weight.

11. The method of claim 1, wherein the composition is administered to the affected tissue via systemic, intratumoral, intradermal, subcutaneous, intraperitoneal, intracavitary, intraocular or intravenous injection, or via topical administration.

12. The method of claim 1, further comprising prior to the treatment a pre-treatment step with a surface penetration assisting agent.

13. The method of claim 1, further comprising treatment with an anesthetic agent.

14. The method of claim 1, wherein the affected tissue is exposed to light in the wavelength region of 300-800 nm.

15. The method of claim 1, wherein the affected tissue is exposed to light either directly or via an optical fiber inserted through a needle.

16. The method of claim 1, wherein the disorder or abnormality of the body is any malignant, pre-malignant or non-malignant abnormality or disorder responsive to photochemotherapy.

17. The method of claim 16, wherein the disorder or abnormality of the body is selected from the group consisting of tumors; skin disorders; and bacterial, viral, or fungal infections.

18. The method of claim 17, wherein the disorder or abnormality of the body is a tumor.

19. The method of claim 1, wherein the affected tissue is selected from the group consisting of skin; conjunctiva; the lining of the mouth, pharynx, oesophagus, stomach, intestines, rectum, and anal canal; the lining of the nasal passages, nasal sinuses, nasopharynx, trachea, bronchi, and bronchioles; the lining of the ureters, urinary bladder, and urethra; the lining of the vagina, uterine cervix, and uterus; the parietal and visceral pleura; the lining of the peritoneal and pelvic cavities, and the surface of the organs contained within those cavities; the dura mater and meninges; and tumors.

20. The method of claim 19, wherein the affected tissue is a tumor.

21. The method of claim 20, wherein the affected tissue is a tumor in a solid tissue.

* * * * *